(12) United States Patent
Ichinose

(10) Patent No.: US 6,943,005 B2
(45) Date of Patent: Sep. 13, 2005

(54) CELLOPHANE AGAR MEDIUM, AND METHOD FOR OBSERVING A MICROBE

(75) Inventor: Akitoyo Ichinose, Nagasaki (JP)

(73) Assignee: Nagasaki University, Nagasaki (JP)

( * ) Notice: Subject to any disclaimer, the term of this patent is extended or adjusted under 35 U.S.C. 154(b) by 0 days.

(21) Appl. No.: 10/683,277

(22) Filed: Oct. 14, 2003

(65) Prior Publication Data

US 2004/0241787 A1 Dec. 2, 2004

(30) Foreign Application Priority Data

May 26, 2003 (JP) .......................................... 2003-147482

(51) Int. Cl.$^7$ ................................................. C12N 1/00
(52) U.S. Cl. ..................... 435/243; 435/294; 435/252.1; 435/255.7
(58) Field of Search ................................ 435/243, 254, 435/395, 404, 252.1, 255.7, 29

(56) References Cited

PUBLICATIONS

A. Ichinose et al.; "An Agar–Coated Cellophane Method for Bacterial Observation Using Scanning and Transmission Electron Microscopy"; Journal of Electron Microscopy Technology for Medicine and Biology; vol. 16, No. 3; 2002; pp 15–20.

Hiroshi Kushida; "New Methods for embedding with low viscosity epoxy resine"; The Cell, 13 (6); 1981; pp 184–188.

Hiroshi Kushida; "An Improved Embedding Method using ERL 4206 and Quetol 653", J. Electron Microsc., vol. 29; No. 2; 1980; pp 193–194.

Kazunobu Amako et al.; "An Improved Method for Observation of Bacterial Growth Using the Scanning Electron Microscope"; J. Electro Microsc., vol. 26, No. 2; 1977; pp 155–159.

Motoyuki Matsuguchi et al.; "Optimal Condition for Observing Bacterial Flagella by the Scanning Electron Microscope"; J. Electro Microsc.; vol. 26, No. 4; 1977; pp 343–344.

Akitoyo Ichinose et al.; Method to observe active interaction between bacteria and cultured cell line; Re evaluation of processing specimen for electron microscope with cellophane film; The Cell; 29, (7); 1997; pp 278–281.

Kenji Tanaka; "Freeze Substitution Method for Microorganisms. II. Fungal Cell"; vol. 21, No. 1; 1986; pp 23–29.

*Primary Examiner*—David M. Naff
*Assistant Examiner*—Deborah K. Ware
(74) *Attorney, Agent, or Firm*—Oliff & Berridge, PLC

(57) ABSTRACT

A cellophane agar medium is made of a cellophane piece with groove portions on at least one surface thereof and a nutritious agar formed on the surface of the cellophane piece via the groove portions. Then, the cellophane agar medium is disposed under wet condition, and a microbe is inoculated and cultivated on the cellophane agar medium. A fixing solution is added to the cellophane agar medium to fix the microbe to the cellophane agar medium. Thereafter, a given sample is made of the cellophane agar medium with the microbe and then, observed with a scanning electron microscope or a transmission electron microscope.

16 Claims, 2 Drawing Sheets

CELLOPHANE AGAR MEDIUM, AND METHOD FOR OBSERVING A MICROBE

BACKGROUND OF THE INVENTION

1. Field of the Invention

This invention relates to a cellophane agar medium which is preferably usable in various fields such as food manufacture, sake brewing, soy manufacture, medicine manufacture, and pollution and hygiene research, and to a method for observing a microbe.

2. Description of the Prior Art

Fungous cell such as mold and yeast can not be fixed well, which is different from zooblast, so that micro structural research and development lag behind conspicuously. In this point of view, it is disclosed in "Microscope, Vol. 21, No. 1, 1986" that a cellophane is disposed so as to be opposite to a agar medium to which a microbe such as fungous cell is inoculated and the resultant cellophane agar medium with the grown hypha is immersed in a cooling medium to freeze and fix the microbe with the cellophane. This fixing method is called as a rapid freezing substitution method.

With the conventional method, however, it is required to sandwich the resultant cellophane agar medium with the microbe with two glass plates. Therefore, it is difficult to make such a sample as to be able to be utilized in scanning electron microscope observation and transmission electron microscope observation. Also, the true configuration of growth and proliferation and the inherent configuration of the microbe can not be observed in situ.

In order to observe the true configuration of growth and proliferation and the inherent configuration of a microbe, it is disclosed in "Monthly cells, Vol. 29, 1997" that the microbe is directly cultivated on a cellophane agar medium. With the conventional method, since a thin sample can be made easily from the resultant cellophane agar medium, such a sample as to be able to be utilized in scanning electron microscope observation and transmission electron microscope observation can be made easily. With the conventional method, however, since the microbe can not be fixed effectively and efficiently onto the cellophane agar medium, it can not be observed practically with the scanning electron microscope or the transmission electron microscope.

SUMMERY OF THE INVENTION

It is an object of the present invention to fix a microbe such as a bacterium in good condition and thus, to realize the in-situ observation for the true configuration of growth and proliferation and the inherent configuration of the microbe with a scanning electron microscope a transmission electron microscope.

In order to achieve the above object, this invention relates to a cellophane agar medium comprising:

a cellophane piece with groove portions on at least one surface thereof, and a nutritious agar formed on the surface of the cellophane piece via the groove portions.

Cellophane is one of celluloses made from viscose. Therefore, even though the cellophane is processed thinner, the mechanical strength of the cellophane is relatively large, so that the cellophane can be easily handled with tweezers. In the present invention, since the groove portions are formed on the at least one surface of the cellophane piece, even though the agar medium is prepared onto the cellophane piece in order to cultivate the microbe, the agar medium can not be broken away. Also, since the agar medium can be formed thinner on the cellophane piece, the microbe to be cultivated can not be damaged by the infiltration of embedding resin.

As mentioned above, in the present invention, the microbe is cultivated by utilizing the cellophane agar medium. Concretely, the cellophane agar medium is located under wet atmosphere, and the microbe is inoculated and cultivated onto the cellophane agar medium. Then, a fixing solution is added to the cellophane agar medium to fix the microbe onto the cellophane agar medium. Then, the fixed microbe is observed with a scanning electron microscope or a transmission electron microscope.

Since the cellophane agar medium can be easily processed thinner, such a micro and thin sample as to be able to be employed in scanning electron microscope observation or transmission electron microscope observation can be made easily from the cellophane agar medium. Also, since the microbe is cultivated directly onto the cellophane agar medium under the wet atmosphere, the true configuration of growth and proliferation and the inherent configuration of the microbe can be observed with the scanning electron microscope or the transmission electron microscope from the micro and thin sample.

BRIEF DESCRIPTION OF THE DRAWINGS

For better understanding of the present invention, reference is made to the attached drawings, wherein.

DESCRIPTION OF THE PREFERRED EMBODIMENTS

This invention will be described in detail with reference to the accompanying drawings. In a cellophane agar medium according to the present invention, groove portions are formed on at least one surface of a cellophane piece to be employed. The depth of the groove portions is not restricted, but preferably set to 1 $\mu$m or over. The surface density of the groove portions on the cellophane piece is preferably set to $3 \times 10^4/\text{cm}^2$ or over. In this case, the anchor effect of the cellophane piece is enhanced, so that a nutritious agar to be formed later can be easily sustained.

The shape of the groove portions is not restricted, and depends on the forming method thereof.

The groove portions can be formed by means of ion etching utilizing e.g., ion-sputtering apparatus. In this case, the surface of the cellophane piece is bombarded with ions to be rendered concave-convex shape. Therefore, the groove portions are constructed of the concave portions of the bombarded surface of the cellophane piece.

If the surface of the cellophane piece is abraded with an iron and steel brush, the groove portions can be made mechanically in linear shape.

The cellophane is appropriately processed in advance so as to be easily handled with tweezers, for example. Concretely, the length of one edge of the cellophane piece is preferably set within 5–8 mm. Also, the thickness of the cellophane piece is preferably set within 37–60 $\mu$m.

Then, the nutritious agar is prepared onto the processed surface with the groove portions of the cellophane piece. The nutritious agar may be made as follows. First of all, a given liquid agar is prepared and the cellophane piece is immersed into the liquid agar. Then, the thus adhered agar on the surface of the cellophane piece is cooled and solidified in e.g., a refrigerator to complete the nutritious agar on the surface of the cellophane piece. In this case, the cellophane piece may be sterilized with ethylene oxide gas or the like, and the liquid agar may be sterilized in an autoclave.

The thickness of the nutritious agar is not restricted, but preferably made thinner so that the infiltration of embedding resin, which is employed in the subsequent formation process of a sample for microscope observation, and thus, the damage for the microbe to be cultivated can be prevented. Concretely, the thickness of the nutritious agar is preferably within 2–5 μm.

Figure 1:
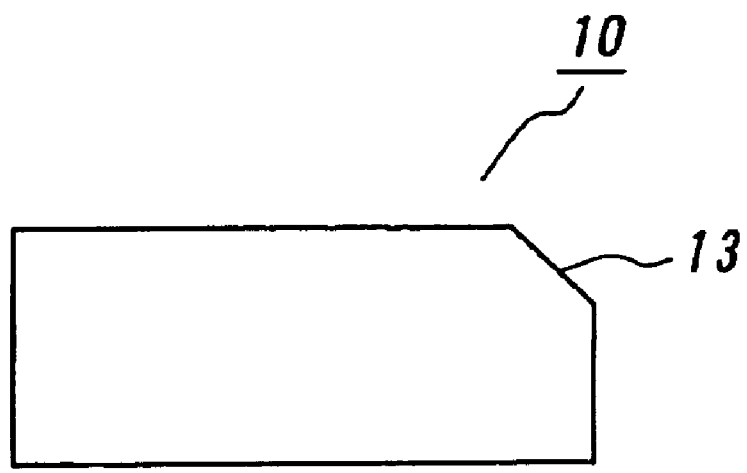
FIG. 1 is a top plan view showing a cellophane agar medium according to the present invention.
Figure 2:
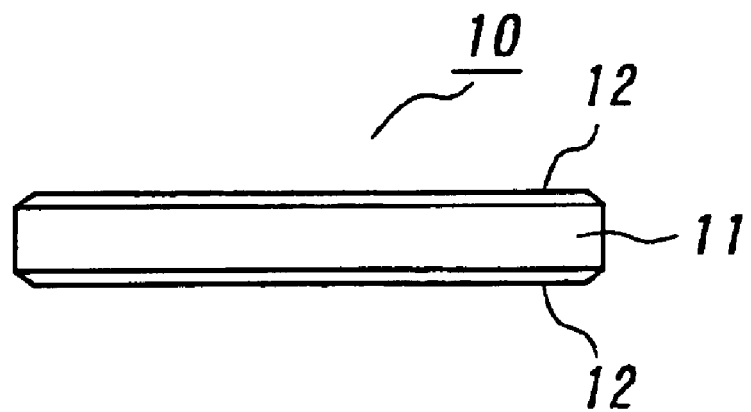
FIG. 2 is a side view of the cellophane agar medium shown in FIG. 1.

FIGS. 1 and 2 are structural views showing a cellophane agar medium fabricated by the above-mentioned process, according to the present invention. FIG. 1 is a top plan view showing the cellophane agar medium, and FIG. 2 is a side view of the cellophane agar medium shown in FIG. 1.

With the cellophane agar medium of this embodiment, the nutritious agars 12 are formed on both surfaces of the cellophane piece 11. The right upper edge of the cellophane agar medium 10, that is, the cellophane piece 11 is cut off to form the notch 13. With the notch 13, the front surface or the rear surface of the cellophane agar medium 10 can be easily determined.

The position of the notch is not particularly restricted, but preferably set at the edge portion of the cellophane piece 11, as mentioned above. In this embodiment, therefore, the front surface or the rear surface of the cellophane piece 11 can be easily determined, as mentioned above.

Next, a method for observing a microbe utilizing the above-mentioned cellophane agar medium will be described.

Figure 3:
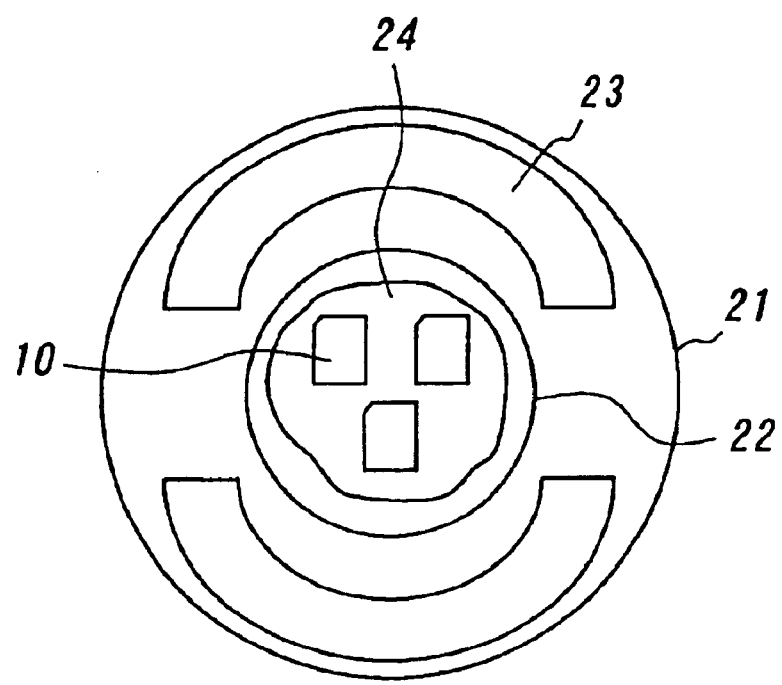
FIG. 3 is a plan view showing a cultivating state of a microbe utilizing the cellophane agar medium of the present invention.
Figure 4:
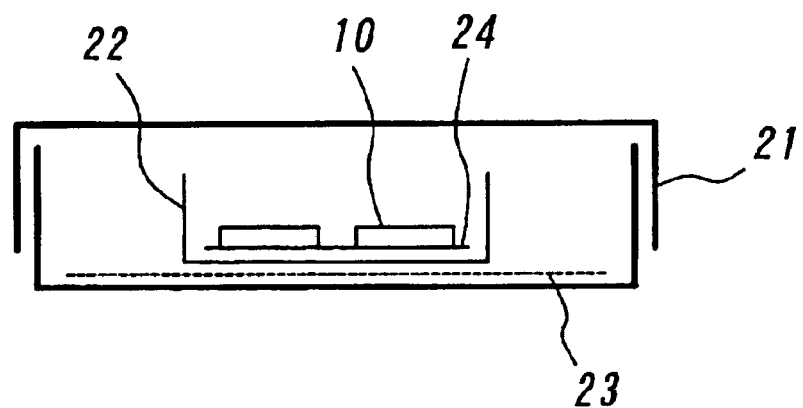
FIG. 4 is a side view of the cultivating state shown in FIG. 3.

FIGS. 3 and 4 are explanatory views for the cultivating method of microbe utilizing the cellophane agar medium. FIG. 3 is a top plan view showing the cultivating state of the microbe, and FIG. 4 is a side view of the cultivating state shown in FIG. 3.

With the cultivating the microbe, as shown in FIGS. 3 and 4, the covered petri dish 21 as an airtight container and the non-covered petri dish 22 are prepared, and the filter paper 23 with moisture is disposed at the bottom of the covered petri dish 21. The non-covered petri dish 22 is disposed into the covered petri dish 21, and the film 24 is disposed at the bottom of the non-covered petri dish 22. Then, the cellophane agar medium 10 is disposed onto the film 24.

Since the cellophane agar medium 10 is disposed in the non-covered petri dish 22, and thus, not contacted directly with the filter paper 23, the direct infiltration of the moisture of the filter paper 23 into the cellophane agar medium 10 can be prevented.

Then, the microbe is inoculated onto the cellophane agar medium 10 and held at a predetermined temperature to be cultivated. Since the cellophane agar medium 10 is disposed into the covered petri dish 21 and closed therein, the interior of the covered petri dish 21 is wet, so that the cultivating process of the microbe is performed under the wet condition. In this case, the dehydration of the microbe can be prevented.

With the cultivating a bacterium as the microbe, it is desired that the bacterium is suspended at a concentration within $10^8$–$10^9$ cfu/mL in a raw dietary water such as a physiological saline, and the thus obtained suspension is inoculated onto the cellophane agar medium 10.

After the culture, the cellophane agar medium 10 is transferred to another container such as a weighing bottle, and a fixing solution such as a glutaric aldehyde solution is injected at a predetermined concentration to preliminarily fix the microbe onto the cellophane agar medium 10. Then, the fixing solution is injected additionally to fix the microbe onto the cellophane agar medium 10 perfectly. Then, the cellophane agar medium 10 is dehydrated and dried at critical point, and subsequently, coated with Au—Pd to be provided as a sample for scanning electron microscope observation.

With the cultivating the bacterium, hypotonic cacodylic buffer solution or NaCl is added to the fixing solution to prevent the shrinkage of the bacterium on the cellophane agar medium. In this case, the almost true configuration of the bacterium can be observed.

With transmission electron microscope observation, the fixed and dehydrated cellophane agar medium 10 is cut into minute pieces without breakaway, each with a size of 1×5 mm$^2$, and the resultant minute pieces are immersed into anhydrous acetone and propylene oxide and infiltrated with low viscosity epoxy resin. Moreover, a gelatine capsule is prepared, and the dehydrated cellophane agar medium 10 is inserted into the capsule and infiltrate with low viscosity epoxy resin. In the latter case, the capsule with the agar is prepared for transmission electron microscope observation.

In the infiltrating process, the minute pieces of the cellophane agar medium 10 are immersed into a mixture of the low viscosity epoxy resin and the propylene oxide, and vibrated therein to infiltrate the epoxy resin the minute pieces through the polymerization at a predetermined temperature. This infiltrating process is called as Quetol 653 method, which is described in detail in "Low viscosity epoxy resin embedding method, Cells 13, 1981, p184–188, by H. kushida" and "A new method for embedding with low viscosity epoxy resin, Quetol 653, J. Electron. Microsc. 29, p193–197, by H. Kushida."

Then, the very thin piece is cut in a thickness of about 80 nm out of the minute piece, and a carbon film is deposited onto the thin piece. The resultant sample can be provided as a sample for the transmission electron microscope observation.

Since the above-mentioned sample for the scanning electron microscope observation or the transmission electron microscope observation is obtained through the culture on the cellophane agar medium 10 under the wet condition, the true configuration of growth and proliferation and the inherent configuration of the microbe can be observed with the scanning electron microscope or the transmission electron microscope.

Although the present invention was described in detail with reference to the above examples, this invention is not limited to the above disclosure and every kind of variation and modification may be made without departing from the scope of the present invention.

As mentioned above, according to the present invention, a microbe such as a bacterium can be fixed in good condition and thus, the in-situ observation for the true configuration of growth and proliferation and the inherent configuration of the microbe can be realized with a scanning electron microscope or a transmission electron microscope. Concretely, since the microbe is cultivated under wet condition, the proliferation of the flagellum and ciliation which are inherent to a bacterium can be observed.

Also, a plurality of cellophane agar media can be prepared, so that a plurality of samples can be prepared. In this case, for example, the proliferation process of a bacterium can be observed with time. Moreover, a sample for scanning electron microscope observation or transmission electron microscope observation can be provided simultaneously.

What is claimed is:

1. A cellophane agar medium comprising:
   a cellophane piece with groove portions on at least one surface thereof, the cellophane piece defining an edge that is cut to form a notch; and
   a nutritious agar formed on said surface of said cellophane piece via said groove portions, wherein a depth of said groove portions is 1 μm or over, and a surface density of said groove portions is $3 \times 10^4/\text{cm}^2$ or over.

2. The cellophane agar medium as defined in claim 1, wherein said groove portions are formed by means of ion etching.

3. The cellophane agar medium as defined in claim 1, wherein said groove portions are formed by means of mechanical abrading.

4. The cellophane agar medium as defined in claim 1, wherein a thickness of said nutritious agar is within 2–5 μm.

5. The cellophane agar medium as defined in claim 1, which is utilized for scanning electron microscope observation.

6. The cellophane agar medium as defined in claim 1, which is utilized for transmission electron microscope observation.

7. A method for observing a microbe, comprising the steps of:
   disposing a cellophane agar medium as defined in claim 1 under wet condition,
   inoculating and cultivating said microbe on said cellophane agar medium,
   adding a fixing solution to said cellophane agar medium to fix said microbe to said cellophane agar medium, and
   observing said microbe with a scanning electron microscope.

8. The observing method as defined in claim 7, wherein said microbe is suspended in a raw dietary water, and the thus obtained suspension is inoculated on said cellophane agar medium.

9. The observing method as defined in claim 8, wherein a concentration of said suspension is set within $10^8$–$10^9$ cfu/mL.

10. The observing method as defined in claim 7, wherein said cellophane agar medium is disposed in a given airtight container, and said wet condition is formed by disposing a filter paper with moisture in said airtight container.

11. The observing method as defined in claim 10, wherein said cellophane agar medium is disposed in another container provided in said airtight container so as not to be contacted with said filter paper.

12. A method for observing a microbe, comprising the steps of:
   disposing a cellophane agar medium as defined in claim 1 under wet condition,
   inoculating and cultivating said microbe on said cellophane agar medium,
   adding a fixing solution to said cellophane agar medium to fix said microbe to said cellophane agar medium, and
   observing said microbe with a transmission electron microscope.

13. The observing method as defined in claim 12, wherein said microbe is suspended in a raw dietary water, and the thus obtained suspension is inoculated on said cellophane agar medium.

14. The observing method as defined in claim 13, wherein a concentration of said suspension is set within $10^8$–$10^9$ cfu/mL.

15. The observing method as defined in claim 12, wherein said cellophane agar medium is disposed in a given airtight container, and said wet condition is formed by disposing a filter paper with moisture in said airtight container.

16. The observing method as defined in claim 15, wherein said cellophane agar medium is disposed in another container provided in said airtight container so as not to be contacted with said filter paper.

* * * * *